US00PP09255P

United States Patent [19]

Goffreda

[11] Patent Number: Plant 9,255

[45] Date of Patent: Aug. 22, 1995

[54] APRICOT TREE 'NJA53'

[75] Inventor: Joseph C. Goffreda, Kendall Park, N.J.

[73] Assignee: Rutgers University, New Brunswick, N.J.

[21] Appl. No.: 978,428

[22] Filed: Nov. 18, 1992

[51] Int. Cl.[6] ..... A01H 5/00

[52] U.S. Cl. ..... Plt./39

[58] Field of Search ..... Plt. 39

*Primary Examiner*—Howard J. Locker
*Assistant Examiner*—Elizabeth C. Kemmerer
*Attorney, Agent, or Firm*—Frank B. Robb; Robb & Robb

[57] ABSTRACT

A new Apricot Tree cultivar producing very early maturing fruit of very good dessert quality.

1 Drawing Sheet

BACKGROUND OF THE DISCLOSURE

This invention relates to a new and distinct cultivar of Apricot Tree, discovered near Cream Ridge, N.J., as part of an extensive program to develop improved apricot trees having early maturing fruit of excellent dessert quality.

The cultivar of this invention is a seedling whose parentage is known and selected from a block planted near Cream Ridge, N.J., in a cultivated area of other trees whose breeding records are also kept.

The new cultivar which I have chosen to designate as NJA53, was produced by crossing a seedling known as RR17-62, being the seed parent, and another selection, NJA13, being the pollen parent, neither of which is patented.

I have found during continued growth of the trees of this cultivar, that it produces a vigorous, moderately spreading tree with good crops.

The tree flowers at or about one day later than the cultivar known as "Harcot" (unpatented) in the area of Cream Ridge, N.J., and the apricot fruit produced has very good quality, especially for its ripening season.

During the course of the several years of observing the growth it is noted that the selection was asexually propagated by grafting on peach rootstock in the vicinity of Cream Ridge, N.J.

The selected tree was of grafted material and is an example of those which have maintained the desired characteristics after propagation in successive generations.

Figure 1:
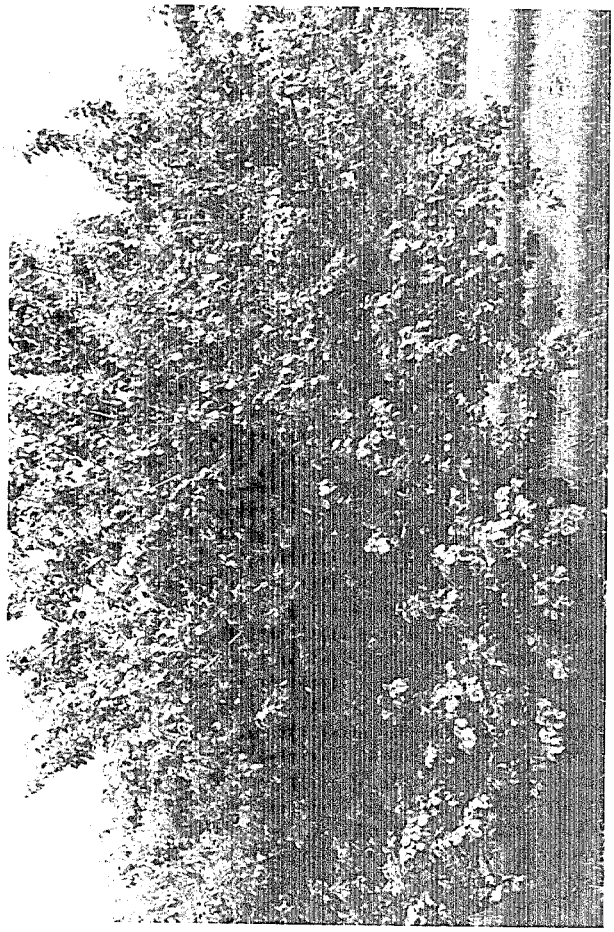

In support of the disclosure herein, the drawing included, in FIG. 1 shows a typical example of young trees of the new cultivar illustrating the growth habit.

Figure 2:
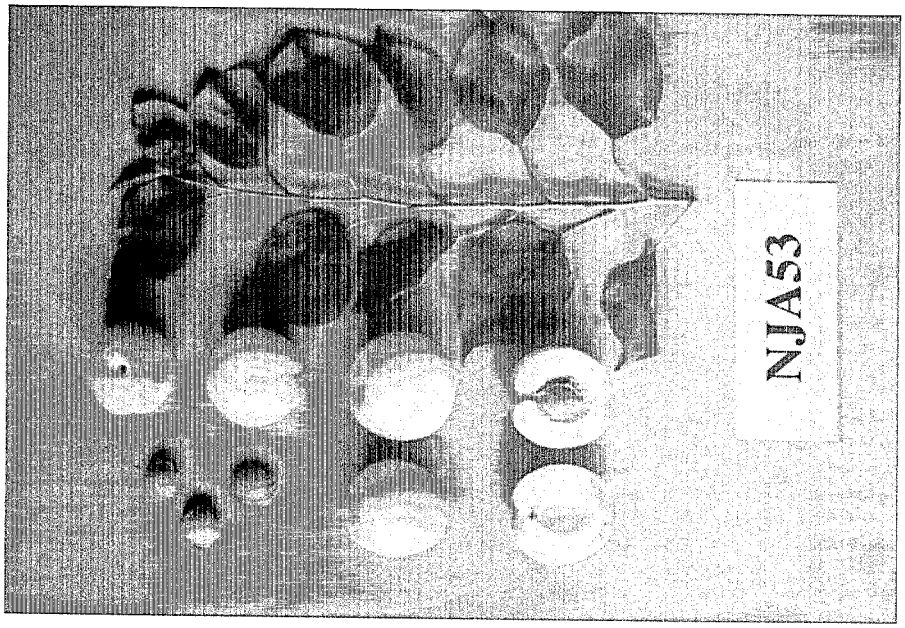

FIG. 2 shows a typical example of the apricot produced, disclosing the color, globose, slightly compressed shape, flesh color, and blush with the skin color as well as typical examples of the seeds and leaves, disclosing their color and shape.

In describing the tree and fruit in particular detail, reference is had to the Horticultural Color Chart issued by the British Color Council in collaboration with the Royal Horticultural Society. Color was also measured in terms of its color space coordinates (L*a*b) with a Minolta CR-300 Croma Meter calibrated with a white calibration plate. The photographs forming the drawing herein are as nearly like the actual fruit and tree as it is possible to make the same in a color reproduction of this kind.

Turning to the details of this new cultivar, I note that the following detailed description embodies the primary distinctive characteristics and identifying means by which the tree is recognized and the fruit produced is described.

Fruit

Shape: Globose, slightly compressed.

Average size: Axial diameter 4.7 cm (1.85 inches); transverse diameter in suture plane 4.8 cm (1.89 inches); transverse diameter at right angles to suture plane 4.6 cm (1.81 inches).

Average mass; 54.1 g.

Skin color: Undercolor is spanish orange Plate 26a (L=62.15 a=+12.82 b=+45.50). Overcolor is orange-red (L=47.11; a=+25.35; b=+28.26). The percentage of red blush over the surface of the fruit will vary with the amount of direct exposure to sunshine. The percentage may vary from 0–50% but an average may be said to be about 30%. The blush is in the orange-Red Group between Plates 34a and 34b RHS Colour Chart.

Pubescence: Slight.

Suture: Shallow. Extends from base to apex. Slightly more pronounced at stem end.

Base: Retuse.

Apex: Rounded to slightly depressed, pistil point slightly depressed.

Cavity: Elongated; average width 1.3 cm (0.5 inches at right angle to suture plane; average width 2.2 (0.875 inches) in sutute plane; average length 2.6 cm (1 inch).

Maturity: Ripens approximately 2 weeks prior to the cultivar "Harcot" when grown at Cream Ridge, N.J. The date of ripening of fruit produced varies with the location in which the tree is grown and the season. At the area near Cream Ridge, N.J., the ripe date has varied from June 7 to June 22 but usually ripens on or about June 19, which is 14 days before the unpatented cultivar "Harcot" ripens usually.

Use: Early maturing, very good quality, dessert apricot.

Flesh

Thickness: Medium.

Color: Orange Plate 24b.

Texture: Melting.

Firmness: Moderately firm, softens at apex.

Eating quality: Very good.

The skin of this new variety is acidic when the fruit is firm ripe, the flesh being sweet. As the fruit softens, the acidity in the skin decreases rapidly. Fully ripened fruit is sweet and mild. When properly thinned, the fruit has moderate apricot flavor and aroma. When the flesh of fully ripened fruit becomes soft it is very juicy. The dessert quality is good.

The fruits ripen slightly unevenly on the tree and will usually require two picking dates about one week apart. Softening of the individual fruit is slightly uneven with more rapid softening at the tip of the fruit. It maintains its quality in cold storage for about 2 weeks. The fruit is not normally stored on the tree.

Stone

Type: Freestone.
Shape: Ovid.
Size: Small to medium. Average length 2.4 cm (0.9) inches); average width 2.1 cm (0.8 inches).
Ridges: Slight ridges extending along both sides of the suture plane.
Tendency to split: None.
Surface: Irregular, slightly pitted.
Color: Golden buff to golden brown Plate 164a to 164b (L=52.82; a=10.41; b=+31.37).

Tree

Size: Large.
Vigor: Vigorous.
Growth: Moderately spreading.
Production: Productive.
Bearer: Regular.

Bark color of ½ inch diameter limb is Attic Rose; Plate 178a.

Internode length is variable from 1/16″ at the base of short branches (spurs) to 1⅜″ at the mid-section of long brances (water sprouts). Branching density is average, however this variety forms numerous short branches (fruiting spurs) on two year old wood.

Leaves

Average size: Length 8.7 cm (3.4 inches); width 6.8 cm (2.7 inches).
Form: Ovate, abruptly acuminate, obtuse at base.
Thickness: Medium.
Margin: Serrate.
Color: Adaxial surface green Plate 137a (L=38.07; a=12.01; b=+18.64); abaxial surface yellow green Plate 147b (L=44.82; a=12.40; b=+18.01). The color of young rapidly growing leaves is in the Grayed-Red Group; Plate 181a. Mature leaf color is as described. The red color in the petiole of young leaves does not have any accurately evaluated variable coloring but varies very substantially both between and within the same.
Petiole: Average length 3.3 cm (1.3 inches); average thickness 0.15 cm (0.06 inches).
Glands: Form globose; average number 3.3; variable in number (0–5), primarily found on petiole.

Flowers

Mature flowers may be described as follows:

Size of the flower: Medium.
Position of stigma as compared with anthers: Above.
Shape of petal: Circular.

I claim:

1. A new and distinct Apricot Tree cultivar, substantially as herein shown and described, characterized particularly as to novelty by the vigorous, moderately spreading growth habit of the tree, on peach rootstock, good crop production, very good dessert quality of the fruit which matures very early, and is globose, slightly compressed in shape.

* * * * *